United States Patent [19]

Krauss et al.

[11] Patent Number: 4,869,239

[45] Date of Patent: Sep. 26, 1989

[54] DEVICE FOR LOCATING AND DISINTEGRATING CONCRETIONS IN BODILY CAVITIES

[75] Inventors: Werner Krauss, Maulbronn; Helmut Wurster, Oberderdingen, both of Fed. Rep. of Germany

[73] Assignee: Richard Wolf GmbH, Knittlingen, Fed. Rep. of Germany

[21] Appl. No.: 888,715

[22] Filed: Jul. 24, 1986

[30] Foreign Application Priority Data

Sep. 13, 1985 [DE] Fed. Rep. of Germany ....... 3532678

[51] Int. Cl.$^4$ ............................................. A61B 17/22
[52] U.S. Cl. ..................................... 128/24 A; 128/328
[58] Field of Search ..................... 128/660, 24 A, 328, 128/660.03

[56] References Cited

U.S. PATENT DOCUMENTS 3,990,296 11/1976 Erikson ................................. 128/660
4,347,850 9/1982 Kelly-Fry et al. ................... 128/660
4,610,249 9/1986 Makofski et al. .................... 128/328
4,630,607 12/1986 Duinker et al. ..................... 128/24 A
4,705,026 11/1987 Chaussy et al. ...................... 128/328

FOREIGN PATENT DOCUMENTS 3220751 12/1983 Fed. Rep. of Germany ...... 128/328

Primary Examiner—Ruth S. Smith
Attorney, Agent, or Firm—Willian Brinks Olds Hofer Gilson & Lione

[57] ABSTRACT

A device for locating and disintegrating concretions and stones in bodily cavities by means of a shock wave generator comprises a reclining surface for the patient, with an opening therein below which the generator, including a flexible precursor section, is so arranged that the fluid sealed off from the outside is in contact via the opening with the body section to be treated, either directly or indirectly via a diaphragm sealing off the precursor section. To this end, the reclining surface and the shock wave generator are displaceable with respect to each other.

17 Claims, 5 Drawing Sheets

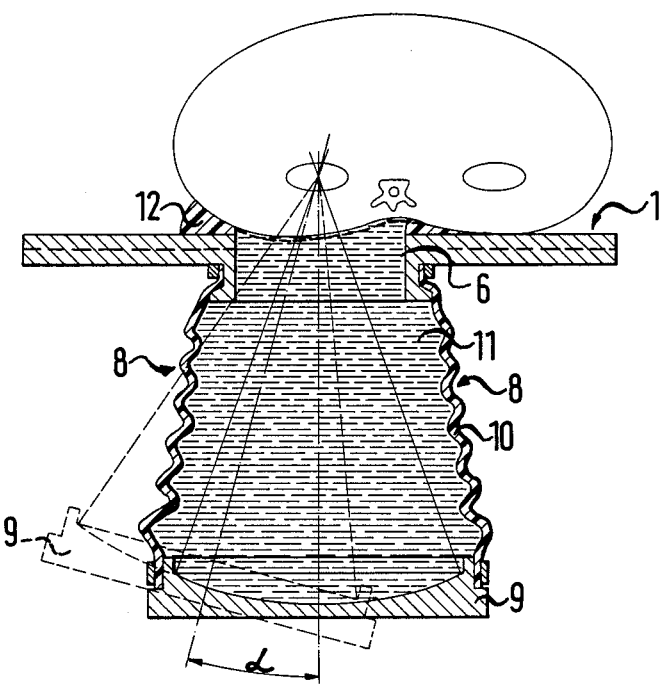
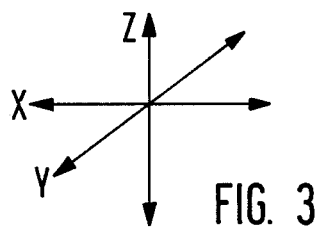
FIG. 3

DEVICE FOR LOCATING AND DISINTEGRATING CONCRETIONS IN BODILY CAVITIES

BACKGROUND OF THE INVENTION

The invention relates to a device for locating and disintegrating concretions and stones in bodily cavities by means of a shock wave generator, from which shock waves are transmitted to the stone enclosed in the body via a coupling fluid in a flexibly constructed precursor fluid section, said fluid being in direct contact with the patient's body.

DESCRIPTION OF THE PRIOR ART

European patent 0084093 discloses a reclining support carrying a patient which may be dipped into a tub or bath filled with coupling fluid. A shock wave generator is then focussed on the concretion or stone which is to be disintegrated.

German patent specification 3220751 discloses a shock wave generator comprising a flexible precursor fluid section and a delimiting foil, for disintegrating stones. With this device, the need for a tub to be filled with a great quantity of fluid is averted, but the flexible precursor section has to be applied to the body manually with the foil and a coupling gel, and held in a particular position.

SUMMARY OF THE INVENTION

It is an object of the invention to provide a device which may be operated easily and conveniently for disintegrating concretions or stones by means of a shock wave generator. It is a further object of the invention to make it possible to move the patient to the setting required for locating and disintegrating a stone, as well as for X-ray verification, without altering his position relative to the patient support.

The first said object is achieved in accordance with the invention in that a reclining surface for the patient is provided with an opening below which a shock wave generator is installed. This shock wave generator comprises a flexible precursor fluid section so installed that its fluid is sealed off in the outward direction. This fluid is placed in direct contact via the opening with the area of the patient's body which penetrates into the opening and is to be exposed to sonic action. Alternately, the fluid in the fluid section may be placed in indirect contact with the same via a precursor section divided into two chambers by means of a diaphragm.

The second said object is achieved in that the patient on the reclining surface may be moved omnilaterally with respect to the stationary shock wave generator (or conversely that the shock wave generator may be moved omnilaterally with respect to the stationary reclining surface) without to this end having to alter the patient's position on the reclining surface. In this way it is possible to obtain any setting required both for locating and disintegrating a stone and for X-ray verification.

By means of the invention, the flexible precursor fluid section of the shock wave generator (which may be of a type known per se) may be connected in a sealed manner to the reclining surface in direct contiguity to the opening and the upper opening rim may have arranged around it a coupling sealing ring which moulds itself in a sealed manner to the body, the area of the body which is to be exposed to sonic action penetrating into the opening, so that it is in direct contact with the fluid in a particularly advantageous manner, or is placed in close-fitting contact with a diaphragm which delimits the precursor section.

Furthermore, the flexible precursor fluid section of the shock wave generator may be connected directly to the patient on the reclining support, the upper edge of the flexible casing of the precursor section being hermetically joined to a bag which extends through the opening and is fastened to the body, advantageously as a belt. In this case too, the area of the body which is to be exposed to sonic action is placed in contact with the fluid of the shock wave generator indirectly via an elastic diaphragm.

Further objects and advantages of the invention will become apparent from the following description, taken in conjunction with the accompanying drawings wherein are illustrated preferred embodiments of the device according to the invention.

BRIEF DESCRIPTION OF THE DRAWINGS

FIG. 3 shows an enlarged axial cross-section through the shock wave generator in conjunction with a reclining surface that supports the patient.

DETAILED DESCRIPTION OF THE PREFERRED EMBODIMENTS

Figure 1:
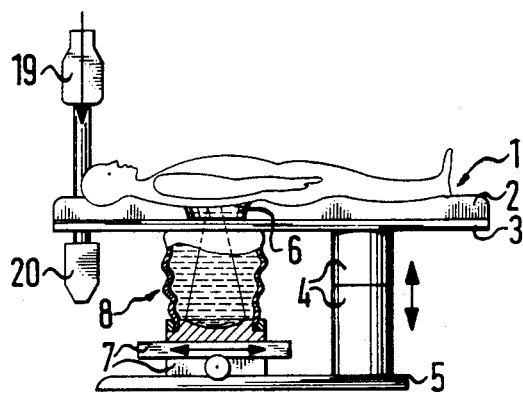
FIGS. 1 and 2 show two sideviews of a device for locating and disintegrating stones within the body of a patient and for X-ray verification thereof, as well as the shock wave generator, in axial cross-section, in alternative positions.

The device for locating and disintegrating concretions in bodily cavities comprises a reclining surface 1 formed by a support 2 for the patient and a reclining table 3, e.g. an operating table, the support 2 being displaceable in two dimensions on the table 3. This reclining surface 1 is supported by a pillar 4 mounted on a base 5 and is provided with an opening 6 on which the body section scheduled for sonic treatment is to be positioned and through which the body section engaged therein is exposed to the sonic action of shock waves to disintegrate a stone therein, by means of a shock wave generator 8, which may be moved and pivotally displaced tridimensionally on a displacing unit 7, and is utilizable in a known manner for locating and disintegrating a stone situated at its focus.

Figure 6:
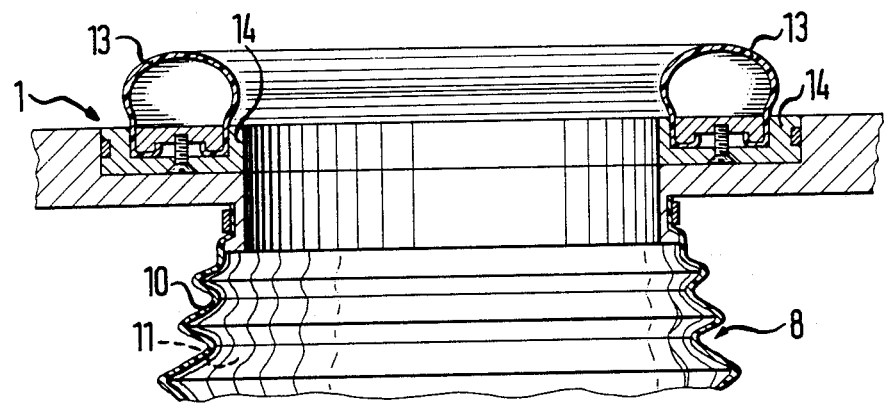
FIGS. 6 and 7 show two enlarged partial cross-sections through the reclining surface, with sealing of the precursor fluid section of the shock wave generator on the patient.
Figure 7:
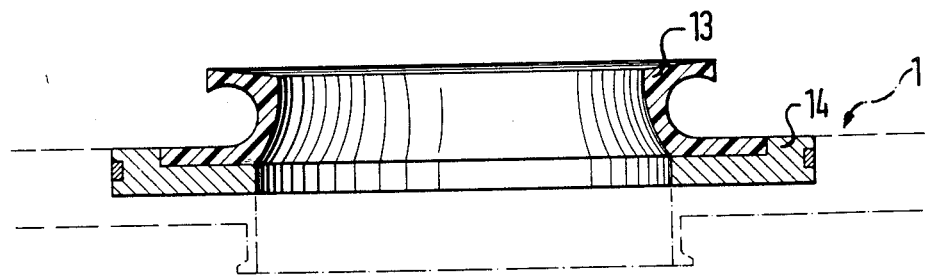

The source 9 of shock waves is surrounded by a flexible casing 10, which is fastened to the reclining surface 1 with the upper extremity sealed around the opening 6, and which is filled with a coupling fluid 11 as a precursor section. The body section scheduled to undergo sonic treatment dips into this fluid via the opening 6, the body section resting on an elastic ring 12 on the reclining surface 1, which seals off the precursor fluid section 11. The seal may also have the form of an annular hose 13 filled with water or gas as shown in FIG. 6 or of an elastic ring 13 as shown in FIG. 7, these seals 13 being exchangeably insertible in the reclining surface 1 by means of a fitting ring 14, depending on the size of the patient.

After the body section to be treated is placed in the area of the opening, the shock wave generator for disintegrating the stone has its focus adjusted on to the stone for location of the same, which is performed by omnilateral displacement of the shock wave generator 8 or of the reclining surface 1. The sonic treatment is particularly advantageous in the case of the embodiment according to FIGS. 1 to 3, since the fluid of the precursor section 11 is then in perfect direct contact with the body section to be treated. It is also possible however for the precursor section 11 to be delimited by a diaphragm or foil (as shown in phantom in FIG. 3) which moulds itself directly to the body or with the interpositioning of an appropriate gel.

Figure 2:
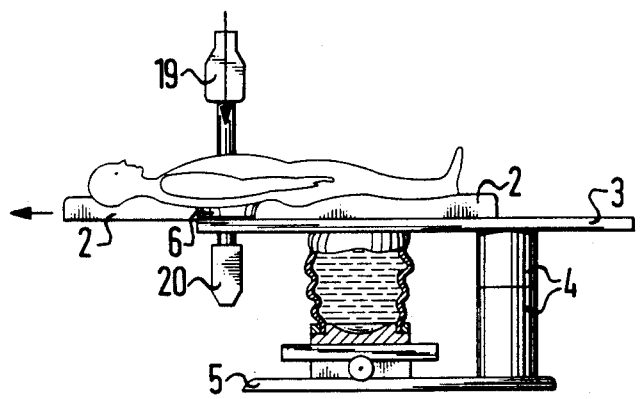
Figure 4:
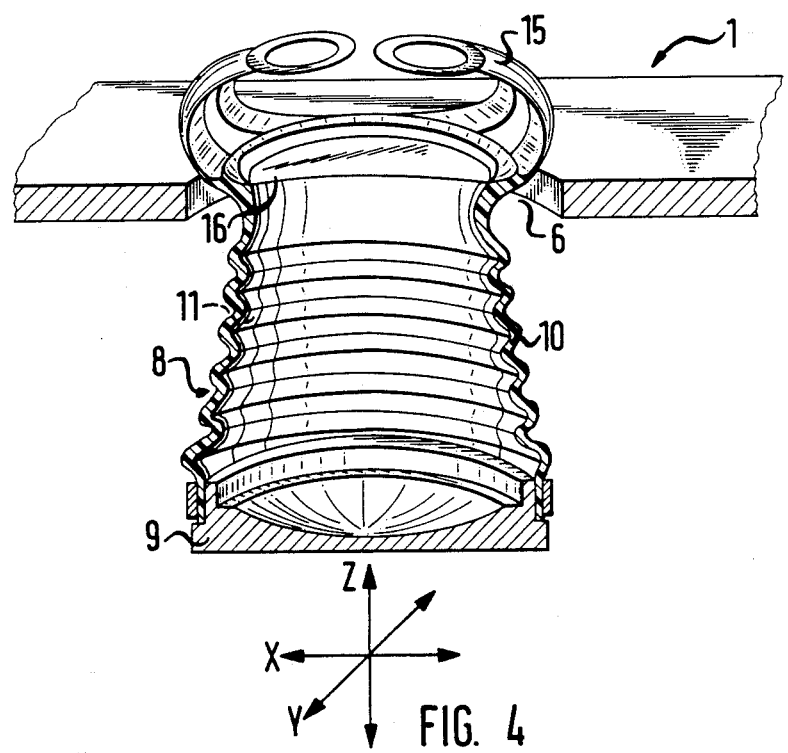
FIG. 4 shows a cross-section of a part of a reclining surface and of a shock wave generator connected directly to the patient.

Instead of the embodiment according to FIGS. 1 to 3, it is also possible to adopt the arrangement shown in FIG. 4, in which the upper edge of the flexible casing 10 of the shock wave generator is joined at its periphery to a belt 15 encircling the patient's body resting on the reclining surface 1, into a unit which projects freely through the opening 6 of the reclining surface 1. In this case, the fluid of the precursor section 11 will be in direct contact with the body section to be treated, or the precursor section 11 is closed off by a thin foil 16, so that a separate space is then formed between the foil 16, the body and the belt 15, which is filled with a fluid coming into contact with the body and forming a complement to the precursor section 11. The adjustment of the focus of the shock wave generator 8 is then performed again by omnilateral adjustment of the shock waves source 9 or of the reclining surface 1 together with the patient, relative to the stationary shock wave generator 8.

Figure 5:
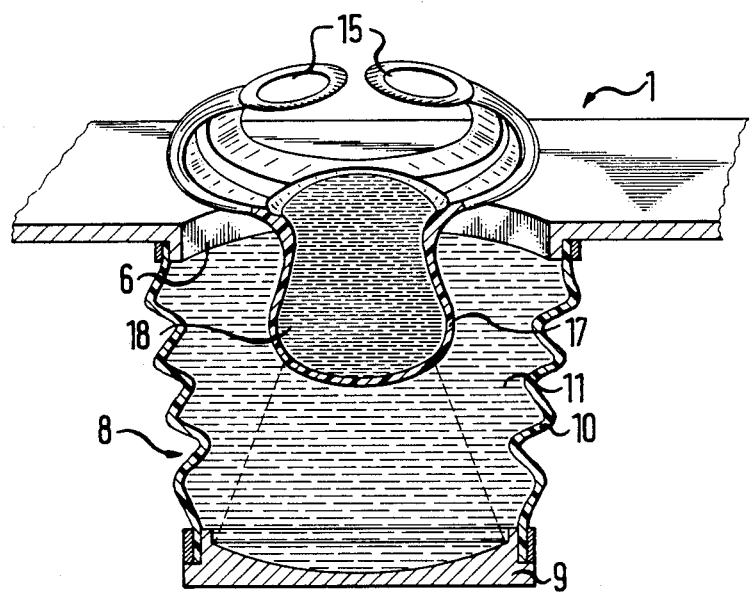
FIG. 5 shows an embodiment similar to that of FIG. 4, but with a modified method of coupling the shock wave generator to the patient's body.

According to FIG. 5, it is also possible for the casing 10 of the precursor fluid section 11 of the shock wave generator 8 to be joined in sealed manner to the reclining surface 1 according to FIG. 3, the level of the fluid 11 ending below the height of the opening 6. In this case, the belt 15 is connected to a bag 17 filled with a coupling fluid 18, which upon placing the belt 15 on the patient is in direct contact with the body section to be treated. On the other hand, this bag 17 dips into the precursor fluid section 11. The adjustment of the focus to the stone which is to be disintegrated is then performed in the manner described in the foregoing. An X-ray check is advantageously performed as soon as a stone has been disintegrated within the body of a patient. An X-ray apparatus 19 is installed at one extremity of the table surface 3 either in freestanding manner or fastened to the table 3, for this check. In the latter case, it is appropriate for the support 2 to be immobilisable in two locked positions on the table 3, of which the one position is determined by the setting of the shock wave generator, and the other position is determined by the setting of the X-ray apparatus 19. In the X-ray check position, the verification is performed by means of an image converter 20 or by means of film exposures.

We claim:

1. A device for locating and disintegrating concretions within body cavities by means of shock waves, said device comprising:
   a support for a patient;
   an opening in said support for location of a part of the patient's body which is to be treated;
   a shock wave generator located below said support and comprising means for generating focussed shock waves;
   a flexibly constructed precursor fluid section coupled to said shock wave generator, said precursor fluid section comprising a flexible casing extending upwardly from the shock wave generator, means for sealing an upper portion of the flexible casing to the periphery of the opening in the support, and a body of coupling liquid contained by the flexible casing and extending upwardly from the shock wave generator toward the support for transmission of shock waves focussed on a concretion from said generator to the concretion;
   a bag containing a coupling fluid; and
   belt means for securing the bag to the patient's body such that the coupling fluid in the bag is placed in direct contact with the patient's body and the bag projects through the opening in the support into contact with the coupling liquid in the flexible casing.

2. The invention of claim 1 wherein the coupling liquid in the flexible casing defines a fluid level below the support.

3. The invention of claim 1 further comprising means for displacing said support and said shock wave generator relative to one another in at least two dimensions.

4. The invention of claim 1 further comprising means for mounting the shock wave generator for pivotable movement about its focal point into an inclined position with respect to the vertical.

5. A device for locating and disintegrating concretions within body cavities by means of shock waves, said device comprising:
   a support for a patient;
   an opening in said support for location of a part of the patient's body which is to be treated;
   a shock wave generator located below said support and comprising means for generating focussed shock waves;
   a flexibly constructed precursor fluid section coupled to said shock wave generator, said precursor fluid section comprising a flexible casing extending upwardly from the shock wave generator, means for sealing an upper portion of the flexible casing to the periphery of the opening in the support, and a body of coupling liquid contained by the flexible casing and extending upwardly from the shock wave generator toward the support for transmission of shock waves focussed on a concretion from said generator to said concretion;
   said flexible casing adapted to allow relative movement between the shock wave generator and the support in at least two dimensions.

6. The invention of claim 5 further comprising means for displacing said support and said shock wave generator relative to one another in at least two dimensions.

7. The invention of claim 5 further comprising means for mounting the shock wave generator for pivotable movement about its focal point into an inclined position with respect to the vertical.

8. The invention of claim 5 further comprising an elastic seal mounted on an upper surface of the support to contact the patient's body, said elastic seal adapted to conform to the patient's body.

9. The invention of claim 5 further comprising a resilient diaphragm mounted to seal the precursor fluid section to adapt itself elastically to the part of the patient's body that is to be treated.

10. The invention of claim 5 wherein said support comprises an operating table and a reclining surface positioned on the table, wherein the opening passes through both the operating table and the reclining surface, and wherein the invention further comprises means for mounting said reclining surface on said table for movement between at least two positions, one selected for disintegrating the concretion within the body part, and the other selected for an X-ray verification.

11. The invention of claim 5 wherein the body of coupling liquid is exposed at the support to allow direct contact between the patient's body and the body of coupling liquid.

12. A device for locating and disintegrating concretions within body cavities by means of shock waves, said device comprising:
   a reclining surface having an opening therein positioned for alignment with a portion of a patient's body which is to be treated;
   a shock wave generator comprising means for generating focused shock waves;
   a flexibly constructed precursor fluid section coupled to said shock wave generator, said precursor fluid section comprising a flexible casing having an upper end fastened to the reclining surface around the opening containing a suitable fluid which couples the shock wave generator with the portion of the patient's body through said opening; and
   an elastic seal disposed on an upper side of the reclining surface, said seal adapted to fit against the patient's body to seal the fluid in the casing.

13. The invention of claim 12, wherein an upper portion of the casing is sealed around the circumference of the opening.

14. The invention of claim 13 further comprising a membrane positioned across the opening and adapted to elastically fit against the portion of the patient's body, said membrane forming an upper boundary of the fluid section.

15. The invention of claim 12 further comprising a membrane positioned across the opening and adapted to elastically fit against the portion of the patient's body.

16. A device for locating and disintegrating concretions within body cavities by means of shock waves, said device comprising:
   a reclining surface having an opening therein positioned for alignment with a portion of a patient's body which is to be treated.
   a shock wave generator comprising means for generating focused shock waves;
   a flexibly constructed precursor fluid section coupled to said shock wave generator, said precursor fluid section comprising a flexible casing having an upper end fastened to the reclining surfaced around the opening and containing a suitable fluid which couples the shock wave generator with the portion of the patient's body through said opening;
   a bag containing a coupling fluid;
   a belt coupled to the bag and adapted to secure the bag to the patient's body such that the coupling fluid is placed in contact with the patient's body and the bag projects through the opening into the precursor fluid section.

17. The invention of claim 16 wherein an upper portion of the casing is sealed around the circumference of the opening.

* * * * *